(12) United States Patent
Anstadt

(10) Patent No.: US 12,263,332 B2
(45) Date of Patent: Apr. 1, 2025

(54) MATERIAL CHARACTERISTICS IDEAL FOR PROVIDING EITHER PARTIAL OR TOTAL MECHANICAL SUPPORT TO THE FAILING OR ARRESTED HEART AND METHOD FOR DEVELOPING IDEAL CHARACTERISTICS FOR UNDERLYING CARDIAC DISORDERS

(71) Applicant: Lifebridge Technologies, LLC, Dayton, OH (US)

(72) Inventor: Mark P. Anstadt, Kettering, OH (US)

(73) Assignee: Lifebridge Technologies LLC, Dayton, OH (US)

( * ) Notice: Subject to any disclaimer, the term of this patent is extended or adjusted under 35 U.S.C. 154(b) by 164 days.

(21) Appl. No.: 18/150,746

(22) Filed: Jan. 5, 2023

(65) Prior Publication Data

US 2024/0091522 A1  Mar. 21, 2024

Related U.S. Application Data

(63) Continuation-in-part of application No. 17/931,853, filed on Sep. 13, 2022.

(51) Int. Cl.
| | | |
|---|---|---|
| A61M 60/191 | (2021.01) | |
| A61M 60/289 | (2021.01) | |
| A61M 60/178 | (2021.01) | |
| A61M 60/515 | (2021.01) | |
| F15B 15/10 | (2006.01) | |

(52) U.S. Cl.
CPC ........ *A61M 60/191* (2021.01); *A61M 60/289* (2021.01); *A61M 60/178* (2021.01); *A61M 60/515* (2021.01); *F15B 15/103* (2013.01)

(58) Field of Classification Search
CPC .............. A61M 60/191; A61M 60/289; A61M 60/515; A61M 60/468; F15B 15/103
See application file for complete search history.

(56) References Cited

U.S. PATENT DOCUMENTS

| | | |
|---|---|---|
| 2,826,193 A | 3/1958 | Vineberg |
| 2,889,780 A | 6/1959 | Binford |
| 3,053,249 A | 9/1962 | Smith |
| 3,233,607 A | 2/1966 | Bolle |

(Continued)

*Primary Examiner* — Pamela M. Bays
(74) *Attorney, Agent, or Firm* — LaMorte & Associates P.C.

(57) ABSTRACT

A system and method for determining the proper dynamic strain profile of an elastomeric construct. The strain characteristics of a deficient heart are determined and compared to the normal strain characteristics of a healthy heart. A construct having elastomeric elements is provided that can expand along multiple axes. In an unloaded condition remote from the deficient heart, the elastomeric elements are pressurized to determine the pressure differential being experienced. Furthermore, optimal strain characteristics are calculated along a first axis and a second axis as a function of the pressure differential. The first optimal strain characteristic and the second optimal strain characteristic are used to estimate the dynamic strain characteristics that will be applied to the heart. The dynamic strain characteristics are compared to the optimal strain characteristics required by the heart to determine if the construct is proper using an automated drive.

16 Claims, 10 Drawing Sheets

(56) References Cited

U.S. PATENT DOCUMENTS

| | | |
|---|---|---|
| 3,279,464 A | 10/1966 | Kline |
| 3,304,501 A | 2/1967 | Ruthenberg |
| 3,371,662 A | 3/1968 | Heid |
| 3,376,863 A | 4/1968 | Kolobow |
| 3,449,767 A | 6/1969 | Bolie |
| 3,455,298 A | 7/1969 | Anstadt |
| 3,478,737 A | 11/1969 | Rassman |
| 3,513,836 A | 5/1970 | Sausse |
| 3,587,567 A | 6/1971 | Schiff |
| 3,590,815 A | 7/1971 | Schiff |
| 3,613,672 A | 10/1971 | Schiff |
| 3,674,381 A | 7/1972 | Schiff |
| 4,048,990 A | 9/1977 | Goetz |
| 4,192,293 A | 3/1980 | Asrican |
| 4,281,669 A | 8/1981 | MacGregor |
| 4,448,190 A | 5/1984 | Freeman |
| 4,536,893 A | 8/1985 | Parravicini |
| 4,609,176 A | 9/1986 | Powers |
| 4,621,617 A | 11/1986 | Sharma |
| 4,662,358 A | 5/1987 | Farrar |
| 4,684,143 A | 8/1987 | Sata |
| 4,957,477 A | 9/1990 | Lundback |
| 4,979,936 A | 12/1990 | Stephenson |
| 5,066,111 A | 11/1991 | Inokuchi |
| 5,089,017 A | 2/1992 | Young |
| 5,098,369 A | 3/1992 | Hellman et al. |
| 5,098,442 A | 3/1992 | Grandjean |
| 5,119,804 A | 6/1992 | Anstadt |
| 5,131,905 A | 7/1992 | Grooters |
| 5,156,154 A | 10/1992 | Valenta, Jr. et al. |
| 5,158,978 A | 10/1992 | Rubin |
| 5,169,381 A | 12/1992 | Snyders |
| 5,199,804 A | 4/1993 | Rimbey et al. |
| 5,205,722 A | 4/1993 | Hammond |
| 5,256,132 A | 10/1993 | Snyders |
| 5,273,518 A | 12/1993 | Lee et al. |
| 5,322,067 A | 6/1994 | Prater |
| 5,330,505 A | 7/1994 | Cohen |
| 5,364,337 A | 11/1994 | Guiraudon et al. |
| 5,368,451 A | 11/1994 | Hammond |
| 5,374,287 A | 12/1994 | Rubin |
| 5,383,840 A | 1/1995 | Heilman et al. |
| 5,385,528 A | 1/1995 | Wilk |
| 5,429,584 A | 7/1995 | Chu |
| 5,476,502 A | 12/1995 | Rubin |
| 5,496,353 A | 3/1996 | Grandjean et al. |
| 5,533,958 A | 7/1996 | Wilk |
| 5,558,617 A | 9/1996 | Heilman et al. |
| 5,562,595 A | 10/1996 | Neisz |
| 5,658,237 A | 8/1997 | Francischelli |
| 5,674,259 A | 10/1997 | Gray |
| 5,697,884 A | 12/1997 | Francischelli et al. |
| 5,697,952 A | 12/1997 | Francischelli et al. |
| 5,707,336 A | 1/1998 | Rubin |
| 5,713,954 A | 2/1998 | Rosenberg et al. |
| 5,716,379 A | 2/1998 | Bourgeios et al. |
| 5,738,627 A | 4/1998 | Kovacs et al. |
| 5,749,839 A | 5/1998 | Kovacs |
| 5,769,800 A | 6/1998 | Gelfand et al. |
| 5,800,334 A | 9/1998 | Wilk |
| 5,861,558 A | 1/1999 | Buhl et al. |
| 5,876,345 A | 3/1999 | Eaton et al. |
| 5,902,229 A | 5/1999 | Tsitlik et al. |
| 5,908,378 A | 6/1999 | Kovacs et al. |
| 5,910,124 A | 6/1999 | Rubin |
| 5,919,209 A | 7/1999 | Schouten |
| 5,971,910 A | 10/1999 | Tsitlik et al. |
| 5,971,911 A | 10/1999 | Wilk |
| 5,980,571 A | 11/1999 | Nomura et al. |
| 6,042,532 A | 3/2000 | Freed et al. |
| 6,044,298 A | 3/2000 | Salo et al. |
| 6,059,750 A | 5/2000 | Fogarty et al. |
| 6,076,013 A | 6/2000 | Brennan et al. |
| 6,095,968 A | 8/2000 | Snyders |
| 6,110,098 A | 8/2000 | Renirie et al. |
| 6,123,726 A | 9/2000 | Mori et al. |
| 6,132,363 A | 10/2000 | Freed et al. |
| 6,183,412 B1 | 2/2001 | Benkowski et al. |
| 6,206,820 B1 | 3/2001 | Kazi et al. |
| 6,224,540 B1 * | 5/2001 | Lederman ............ A61M 60/865 600/37 |
| 6,238,334 B1 | 5/2001 | Easterbrook, III et al. |
| 6,251,061 B1 | 6/2001 | Hastings et al. |
| 6,254,525 B1 | 7/2001 | Reinhardt et al. |
| 6,282,445 B1 | 8/2001 | Reinhardt et al. |
| 6,298,266 B1 | 10/2001 | Rubin et al. |
| 6,309,380 B1 | 10/2001 | Larson et al. |
| 6,328,689 B1 | 12/2001 | Gonzalez et al. |
| 6,408,205 B1 | 6/2002 | Renirie et al. |
| 6,432,039 B1 | 8/2002 | Wardle |
| 6,438,411 B1 | 8/2002 | Guttman et al. |
| 6,464,655 B1 | 10/2002 | Shahinpoor |
| 6,485,407 B2 | 11/2002 | Alferness et al. |
| 6,508,756 B1 | 1/2003 | Kung et al. |
| 6,540,659 B1 | 4/2003 | Milbocker |
| 6,547,716 B1 | 4/2003 | Milbocker |
| 6,572,534 B1 | 6/2003 | Milbocker et al. |
| 6,602,182 B1 | 8/2003 | Milbocker |
| 6,612,978 B2 | 9/2003 | Lau et al. |
| 6,616,596 B1 | 9/2003 | Milbocker |
| 6,622,045 B2 | 9/2003 | Snell et al. |
| 6,626,821 B1 | 9/2003 | Kung et al. |
| 6,641,604 B1 | 11/2003 | Adelman et al. |
| 6,682,474 B2 | 1/2004 | Lau et al. |
| 6,730,016 B1 | 5/2004 | Cox et al. |
| 6,757,561 B2 | 6/2004 | Rubin et al. |
| 6,808,483 B1 | 10/2004 | Ortiz et al. |
| 6,846,296 B1 | 1/2005 | Milbocker et al. |
| 6,971,127 B2 | 12/2005 | Richards |
| 7,331,221 B2 | 2/2008 | Wise et al. |
| 7,494,459 B2 | 2/2009 | Anstadt et al. |
| 7,871,366 B2 | 1/2011 | Criscione et al. |
| 8,187,160 B2 | 5/2012 | Criscione et al. |
| 2003/0032855 A1 | 2/2003 | Shahinpoor |
| 2004/0010180 A1 | 1/2004 | Scorvo |
| 2004/0024315 A1 | 2/2004 | Chalana |
| 2004/0059183 A1 | 3/2004 | Jozef et al. |
| 2004/0078067 A1 | 4/2004 | Thompson et al. |
| 2004/0102674 A1 | 5/2004 | Zadini et al. |
| 2004/0116769 A1 | 6/2004 | Jassawalla |
| 2004/0167375 A1 | 8/2004 | Couvillon |
| 2004/0225177 A1 | 11/2004 | Coleman et al. |
| 2004/0267086 A1 | 12/2004 | Anstadt et al. |
| 2005/0113632 A1 | 5/2005 | Ortiz et al. |
| 2005/0148814 A1 | 7/2005 | Fischi et al. |
| 2005/0234289 A1 | 10/2005 | Anstadt et al. |
| 2006/0142634 A1 | 6/2006 | Anstadt et al. |
| 2006/0167334 A1 | 7/2006 | Anstadt et al. |
| 2006/0211909 A1 | 9/2006 | Anstadt et al. |
| 2007/0197859 A1 | 8/2007 | Schaer et al. |
| 2008/0257412 A1 | 10/2008 | Gordon |
| 2009/0036730 A1 * | 2/2009 | Criscione ............ A61M 60/861 600/37 |
| 2010/0152523 A1 | 6/2010 | MacDonald et al. |
| 2011/0196189 A1 | 8/2011 | Milbocker |
| 2015/0080640 A1 | 3/2015 | Lillehei |
| 2016/0101230 A1 | 4/2016 | Ochsner |
| 2016/0346449 A1 * | 12/2016 | Roche ................ A61M 60/289 |

* cited by examiner

Mock Loaded Material $\longrightarrow$ $\varepsilon_{peak} \approx 0.0481 SA_{ED} + 1.496$ In Vivo Loaded Material $\longrightarrow$ $\varepsilon_{peak} \approx 0.0481 SA_{ED} + 11.064$ Unloaded Material $\longrightarrow$ $\varepsilon_{peak} \approx 0.0481 SA_{ED} + 24.496$

MATERIAL CHARACTERISTICS IDEAL FOR PROVIDING EITHER PARTIAL OR TOTAL MECHANICAL SUPPORT TO THE FAILING OR ARRESTED HEART AND METHOD FOR DEVELOPING IDEAL CHARACTERISTICS FOR UNDERLYING CARDIAC DISORDERS

RELATED APPLICATIONS

This application is a continuation-in-part of U.S. patent application Ser. No. 17/931,853, filed Sep. 13, 2022.

BACKGROUND OF THE INVENTION

1. Field of the Invention

In general, the present invention relates to the methodology of creating and/or selecting an elastomeric construct with the proper dynamic strain profile for a given application within the body. More particularly, the present invention relates to the methods of determining the needed strain profile of an in vivo elastomeric construct, such as an elastomeric construct used in or outside the heart, and matching the strain profile with materials and designs that will provide the needed characteristics.

2. Prior Art Description

In biomedical engineering, strain is a measure of how a material changes length when acted upon by a force. Since a length is a distance between two points in a plane, the measure of strain is relative to the plane in which it occurs. When forces are applied to a three-dimensional object, the forces create strains in multiple planes. The resulting strains created by such forces act in all planes and are referred to as being three-dimensional strains. The three-dimensional strains that occur in a material as a result of an applied force are said to be the strain dynamics of that material.

When acting upon tissue within the body, the strain dynamics supplied by an implanted construct can be either passive or active. Passive strain dynamics occur when the implanted construct is simply imposed or attached to tissue in the body. The implanted construct imposes some resistance to the natural strains of the contacted tissue. On the other hand, active strain dynamics can occur when an implanted construct actively transfers forces to tissue. In such a case, external forces are imposed onto the implanted construct which in turn are transferred to the tissue, therein creating a dynamic strain interaction with the tissue. These forces can be applied to the implanted construct in repetitive cyclic fashion to provide a therapeutic effect on the tissue.

When an implanted construct is used to transfer a force to biologic tissue, the details of the construct's three-dimensional strain dynamics have important implications. Specifically, the strain dynamics of the construct influence the manner in which such forces are transferred to the tissue. Unfavorable strain dynamics can cause adverse consequences such as improper distribution of forces and tissue trauma. Whereas favorable strain dynamics transfer forces as intended without tissue trauma.

A body is filled with various organs, muscles, and other tissue that expand and/or contract. As the organ, muscle, and/or tissue expands and/or contracts, the organ, muscle, and/or tissue undergoes various strains that act in a variety of directions. The conformational, three-dimensional milieu of the various strains can be considered the dynamic strain profile for the organ, muscle, and/or tissue. The strain profile of a certain organ, muscle or tissue can be directly measured by applying strain gauges to such features. Alternatively, the strain profile of a certain organ, muscle or tissue can be measured using data from X-ray scans, MRI scans, ultrasonic scans, or other strain scans that image tissue within the body. Furthermore, for organs like the heart, the dynamic strain profile can be estimated using physical models, virtual models, and/or statistical models.

Given the anatomy, gender, and age of a person, an optimal dynamic strain profile can be readily determined for most any organ, muscle, tissue, or portion thereof. If an organ, muscle, or tissue that is diseased, injured, or damaged, the strain profile of the afflicted organ, muscle, or tissue will differ from the optimal dynamic strain profiles. The issue for the healthcare provider is how to fix the inflicted organ, muscle, or tissue so that the actual dynamic strain profile can better resemble the optimal dynamic strain profile.

In many situations, the dynamic strain profile of an organ, muscle, or tissue can be improved by applying an elastomeric construct to the organ, muscle, or tissue. The elastomeric construct has its own dynamic strain profile. The goal is to select or create an elastomeric construct so that when forces are applied to the construct, the construct will react with a dynamic strain profile that compensates for the deficiencies in the actual dynamic strain profile. Furthermore, the elastomeric construct should embody the ideal surface-to-tissue interaction and/or attachment for the functionality of transferring strain to the organ, muscle, or tissue being affected.

The situation becomes more challenging when the elastomeric construct contains compartments that actively apply forces. For example, an elastomeric heart cuff may be placed outside the ventricles of the heart to assist the heart in contracting and expanding. The physical presence of the heart cuff around the heart has an effect on the heart. Furthermore, in such an application, forces from an external drive are applied to the heart cuff. The structure of the heart cuff and the external drive forces applied to the heart cuff should combine to embody dynamic strain characteristics that affect the heart in a manner that is beneficial to the pumping action of the heart. However, consideration must also be given to maintaining an appropriate surface-to-tissue interaction in order to facilitate the transfer of desired strain characteristics in a non-traumatic fashion and to promote healthy recovery of tissue function.

The actual dynamic strain profile of the functioning heart when pumping blood can be measured. This dynamic strain profile represents a relatively load independent measure of the heart's pumping function. The dynamic strain profile can be used to determine the degree of pumping function and assess the degree of function and/or dysfunction in a variety of disease states. Dynamic strain profiles for optimally functioning hearts can therefore be used as targets when determining the strain therapy needed by diseased hearts.

It is important that heart cuffs and similar devices are constructed of elastomeric materials that embody strain dynamics beneficial to the heart. The heart cuff's mechanical forces should be distributed in a manner that promotes pump function while not harming tissue or negating underlying pump function. A heart cuff's strain profile, when acting on the heart, is dictated by the material characteristics, the resistive forces of the underlying heart, and the therapeutic forces exerted by the drive system. These dynamic forces vary over the entire heart pumping cycle. The forces reverse directionality from augmenting the heart either filling (diastole cycle) versus emptying (systole cycle). The dynamic strain profiles of the heart cuff act in many different dimensions to properly transfer forces to the heart's surface. While these strain profiles may be viewed and/or represented within a single plane or direction, the three-dimensional characteristics of the cuff's strain profile are critical for the proper delivery of mechanical forces to the surface of the heart. Although the elastomeric heart cuff may embody the proper dynamic strain profile in one directional plane it needs to be designed such that it has the proper dynamic strain profiles in all dimensions to optimize the mechanical pump function of the underlying heart. The forces must also impact the heart in a non-traumatic fashion as to avoid injury to the underlying tissue.

An ideal heart cuff must provide the proper dynamic strain characteristics through both the systolic and diastolic cycles of the heart, prevent tissue trauma, and facilitate improved pump function of the dysfunctional and/or non-beating heart. Therefore, the elastomeric construct ideally possesses strain characteristics that meet these requirements. Also, an ideal heart cuff should have a strain profile that can optimize strain dynamics of the functioning myocardium, thereby promoting recovery. This becomes more important when intrinsic heart muscle function is capable of meaningful contraction. When considering both of these requirements, the elastomeric construct used in the heart cuff should provide mechanical pump function to the non-beating, arrested (e.g., ventricular fibrillation) heart while also permitting recovery of underlying myocardial contractile function. Such dynamic strain characteristics of the heart cuff might be considered ideal when mirroring the epicardial surface strain patterns during optimal pump function.

The dynamic strain characteristics of a heart cuff are opposite to the dynamic strain characteristics of the heart muscle during the transfer of mechanical systolic and diastolic forces. The exception is at the end of diastole when the heart reaches maximal diastolic dimensions the elastomer may expand to further expand the ventricular myocardium of the heart. In other words, during systolic force application, the elastomeric heart cuff generally exhibits positive strain as it stretches over the heart. Conversely, during ventricular systole, the heart generally exhibits negative strain as it expels blood and/or the muscle contracts. During diastolic force application, the elastomeric heart cuff exhibits negative strain as it returns to its unstrained position. However, some degree of positive strain may be used in late diastole as the elastomeric heart cuff can further expand the heart. This late diastolic expansion facilitates maximal filling of the heart's end-diastolic capacity, thereby further improving pump function. This is noteworthy when considering that heart cuffs are known to potentially impair diastolic filling of the heart. The heart muscle exhibits positive strain throughout diastole as the ventricular myocardium expands and/or lengthens to accommodate blood entering the heart's chambers.

A need therefore exists for an elastomeric heart cuff and pump that best enables forces to be transferred to the heart to produce ideal ventricular pump function. The elastomer utilized should enable the transfer of mechanical forces that enable the heart muscle to pump in a three-dimensional fashion that results in the optimal pump function. One condition is that of ventricular fibrillation and/or asystole, in which the heart muscle has no intrinsic force generation. Another condition is that in which the heart has some contractile function but requires assistance to adequately pump blood. In both of these conditions, the heart has different underlying characteristic strain patterns. In fibrillation, the heart muscle is being pushed and pulled with strain patterns dictated principally by the force of the heart cuff material and by the underlying resistances of the heart muscle and blood being pumped. In the condition in which the heart has some meaningful pump function, the underlying muscle may pump best when allowed to follow the natural patterns. These contractile patterns of the functioning myocardial cells can be described as a synchronous three-dimensional strain pattern that is distinct from the strain patterns of the asystole or fibrillating heart being mechanically pumped. Notably, the unique properties defined in this disclosure provide material characteristics that allow the underlying heart to optimally pump in either state and provide both systolic (compressive) and diastolic (expansion or dilation) forces that promote the most ideal underlying ventricular strain patterns for pump function while avoiding tissue trauma.

Once an elastomeric construct is discovered that meets the intended criteria for use inside the body, it can be tested in an unloaded condition to best define its physical strain profile. In an unloaded condition outside the body, the elastomeric construct is not in contact with the heart or other tissue that apply the tissue's forces to the construct. Accordingly, an elastomeric construct can be tested under a simpler, controlled or unloaded conditions. Accordingly, one can validate the redesign elements of the elastomeric construct when unloaded. In a loaded condition, the elastomeric construct is in vivo or is attached to a functional model ex vivo which requires load characteristics to be standardized. As such, it is far more difficult to test, and/or validate a desired strain profile under loaded conditions.

There are a variety of elastomeric materials that have been approved for use inside the body. Each of these elastomeric materials have various characteristics that can be selectively adjusted by varying formulations and/or manufacturing variables. The characteristics that can be altered include hardness, tensile strength, tensile modulus, elongation, resilience, compression set, tear resistance, abrasion resistance, and specific gravity. Each of these characteristics effect how the elastomeric material reacts to applied forces. Currently, it is difficult to predict or otherwise model what elastomeric materials will best match the dynamic strain characteristics that must be embodied by a heart cuff. Testing a design in a loaded condition will eventually lead to the design that functions as desired. However, the in vivo setting is not practical for defining the material strain characteristics since the tissue interaction can confound such analyses. Likewise, testing a design in a loaded condition on a lab model uses estimations that may be less than ideal. The best solution is for there to be a way to accurately test an elastomeric construct in an unloaded condition so that the design of the construct can be customized to the particular needs of the condition that the construct has demonstrated effectiveness within the body.

The present invention is an improved method of determining the proper characteristics of an elastomeric construct while in an unloaded condition and selecting the best materials and design to suit the need. This need is met by the present invention as described and claimed below.

SUMMARY OF THE INVENTION

The current invention describes the discovery of an ideal material dynamic strain characteristic for applying mechanical forces to the ventricles of the heart. The discovery includes a means for assessing the material's strain dynamics in a test platform that allows the material characteristics to be reproduced and validated prior to its application for biologic use. The discovery provides a means to further develop related materials for applications in different cardiac disease states.

The present invention is designed for use on hearts of generally normal anatomic proportion and muscle mass with overall normal morphologic proportions but can be translated into hearts of diseased states. The present invention system and method determines the dynamic strain profile of a construct, such as a heart cuff. The dynamic strain profile is used in customizing a heart pump system to the specific needs of a deficient heart. To address the needs of a deficient heart, the strain characteristics of the deficient heart are first determined. The deficient strain characteristics are compared to the normal strain characteristics of a healthy heart to determine any strain discrepancies between the deficient strain characteristics and the normal strain characteristics.

The construct has elastomeric elements that expand along multiple axes when pressurized. The multiple axes include a first axis and a second axis. In an unloaded condition remote from the failing heart, the elastomeric elements are pressurized to determine the pressure differential being experienced. Furthermore, a first optimal strain characteristic is calculated along a first axis and a second optimal strain characteristic along a second axis as a function of the pressure differential.

The first optimal strain characteristic and the second optimal strain characteristic are used to estimate the dynamic strain characteristics that should be embodied by the construct. The dynamic strain characteristics that are estimated for the construct are compared to the optimal strain characteristics required by the failing heart to determine if the construct is proper for use on the failing heart. If the construct is ineffective, features of the construct are altered until the construct can provide the assist required by the heart to achieve a more optimal heart pump function.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Although the present invention system and methodology can be embodied in many ways, only two examples are illustrated and described. The exemplary embodiments being shown are for the purposes of explanation and description. The exemplary embodiments are selected in order to set forth some of the best modes contemplated for the invention. The illustrated embodiments, however, are merely exemplary and should not be considered as limiting when interpreting the scope of the appended claims.

Figure 1:
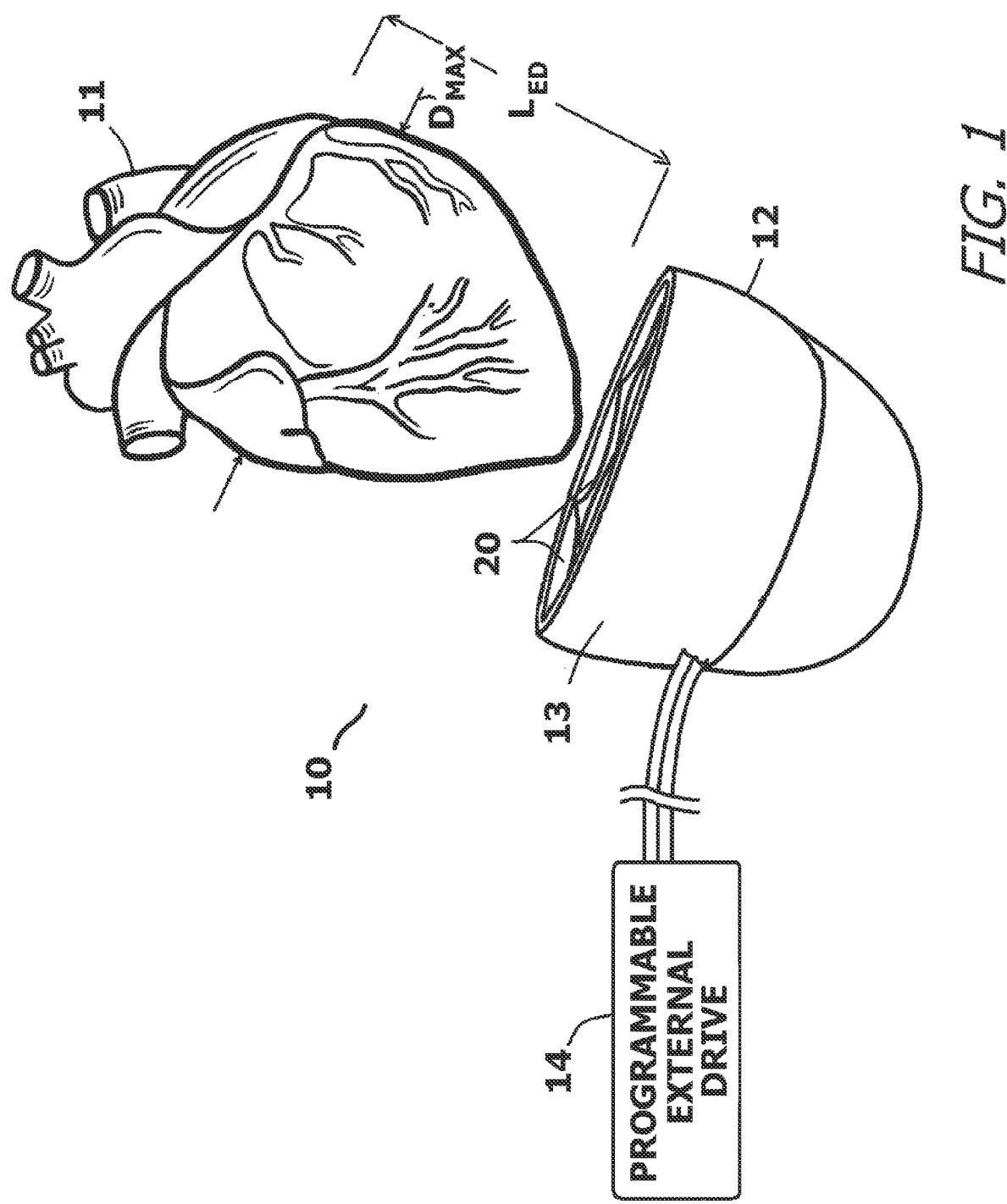
FIG. 1 is a schematic of an exemplary embodiment of a heart pump system showing a heart, a heart cuff, and an external automated drive.

Referring to FIG. 1, a heart pump system 10 is shown that helps a heart 11 pump blood. The heart pump system 10 has an external automated drive 14 that selectively applies positive and negative pneumatic pressure to a heart cuff 12. The heart 11 has measurable dimensions that are unique for a particular individual or condition. One of the measurable dimensions is the maximal diameter of the heart in its short axis ($D_{max}$). The maximal diameter corresponds to the diameter of the myocardium as measured at the end of the diastolic cycle. Likewise, the heart 11 has a measurable length $L_{(ED)}$ that corresponds to the length of the ventricles at the end of the diastolic cycle. These dimensions of the heart 11 can be readily obtained from various medical scanning equipment, such as x-rays, ultrasounds, MRIs, and the like. Furthermore, it is understood that the heart 11 has a heartbeat, wherein the heart 11 contracts with a regular rhythm. Although the rhythm can be irregular, it has a general average rate of contraction over increments of time. The rhythm of the heart 11 can also be quantified using heart monitoring equipment, such as a blood pressure monitor or an ECG unit.

The heart cuff 12 fits outside the ventricles of the heart 11. In the shown embodiment, the heart cuff 12 covers the ventricles of the heart 11. However, other cuff and cup designs can be used that only contact specific areas of the ventricles. The selection of a full cuff or a partial cuff depends upon the needs of the patient. A full cuff, as shown, can apply forces to both the left and right ventricles. A partial cuff or similar device, such as a contact bladder, may only apply forces to one ventricle or part of one ventricle.

Figure 2:
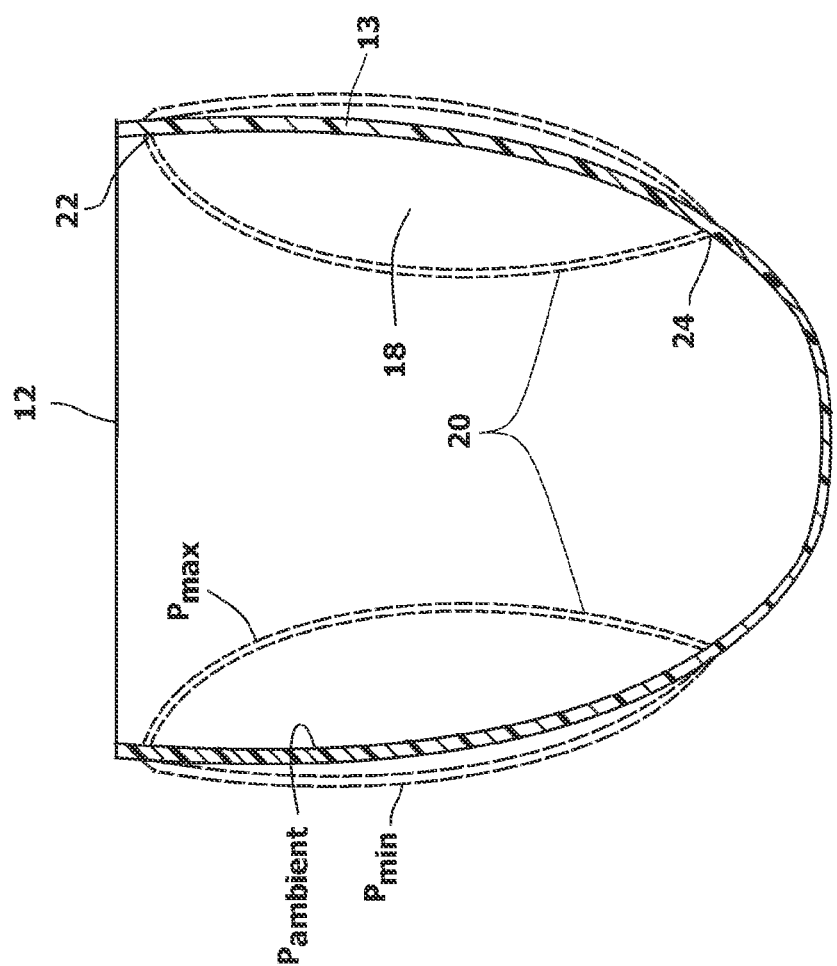
FIG. 2 shows the heart cuff of FIG. 1 in cross-section and in an unloaded condition with indicators of maximum and minimum deflections due to applied pressure differentials.

Referring to FIG. 2 in conjunction with FIG. 1, it will be understood that the exemplary heart cuff 12 being illustrated is made, at least in part, from elastomeric material. The heart cuff 12 is connected to the external automated drive 14 that can cause the heart cuff 12 to selectively contract and expand. The heart cuff 12 has an elastomeric shell 13. Within the shell 13 are a plurality of elastomeric compartment membranes 20. The expansion and contraction actions of the heart cuff 12 are typically created by applying positive and negative pneumatic pressure to various elastomeric compartment membranes 20 embodied or attached within the shell 13.

When the heart cuff 12 is applied to the heart 11, it is considered to be in a loaded condition. That is, the heart cuff 12 is being contacted by the heart 11 and is effected by the various forces applied by the heart 11. In an unloaded condition, the heart cuff 12 is not in contact with the heart 11 or any model of the heart 11. Rather, the heart cuff 12 is free to expand and contract as determined only by the design of the heart cuff 12 and the pressures applied to the heart cuff 12 by the external automated drive 14.

In FIG. 2 the heart cuff 12 is shown in an unloaded condition. As will be explained, the heart cuff 12 is designed, tested, and customized in this unloaded condition. Both the shell 12 of the heart cuff 12 and the elastomeric compartment membranes 20 within the shell 13 have the ability to expand and contract. Due to the design of the heart cuff 12, when the elastomeric compartment membranes 20 are pressurized, they tend to expand inwardly and fold in into relatively defined compartments 18. The compartments 18 are defined between the shell 13 and the compartment membranes 20. Constructs of a heart cuff 12 can be designed such that they comprise only one or multiple compartments 18 depending on how much surface area of the heart 11 in which the cuff 12 intents to act upon.

A basal attachment seam 22 is located at the top of each compartment membrane 20 where the compartment membrane 20 is anchored to the shell 13 of the heart cuff 12. Likewise, an apical attachment seam 24 is located at the bottom of each compartment membrane 20 where the compartment membrane 20 is anchored to the shell 13 of the heart cuff 12. Between the basal attachment seam 22 and the apical attachment seam 24, the compartment membrane 20 is free to expand and contract in an elastic manner. For a heart cuff sized for an average person, the surface area of compartment membranes that is free to expand and/or contract over the majority of the entire heart's outer surface is approximately 220 square centimeters, +/−55 square centimeters.

Figure 3:
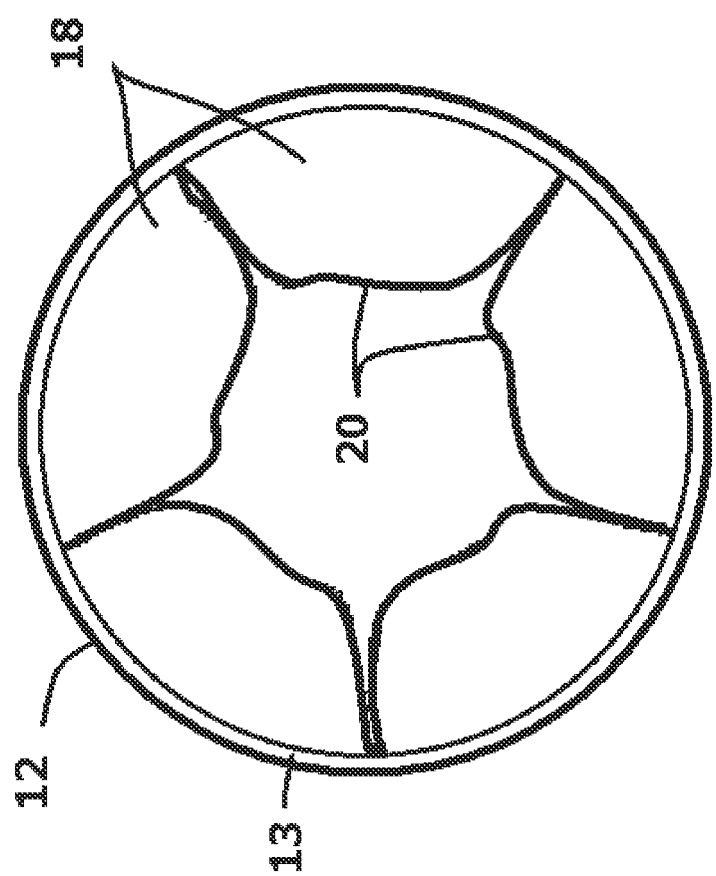
FIG. 3 shows the heart cuff of FIG. 1 from above, unloaded and in a state of maximum positive pressure inflation and producing inflated compartments.
Figure 4:
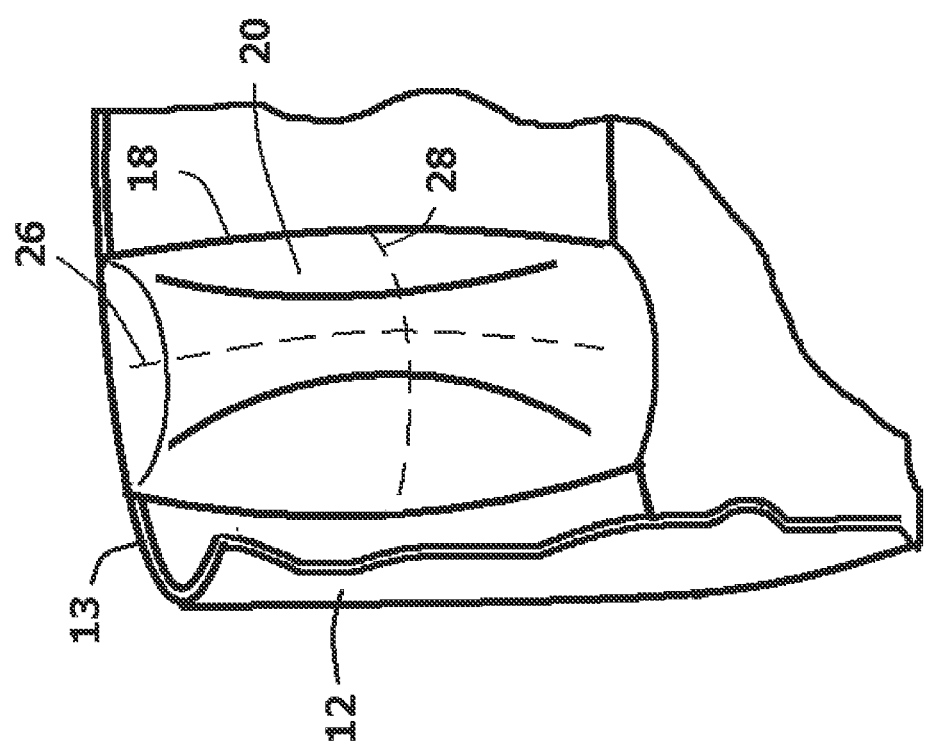
FIG. 4 is a heart cuff illustrated by a transection of the long axis and the short axis on a compartment membrane this serves to illustrate how partial cuffs can be used to support a more limited select area.
Figure 5:
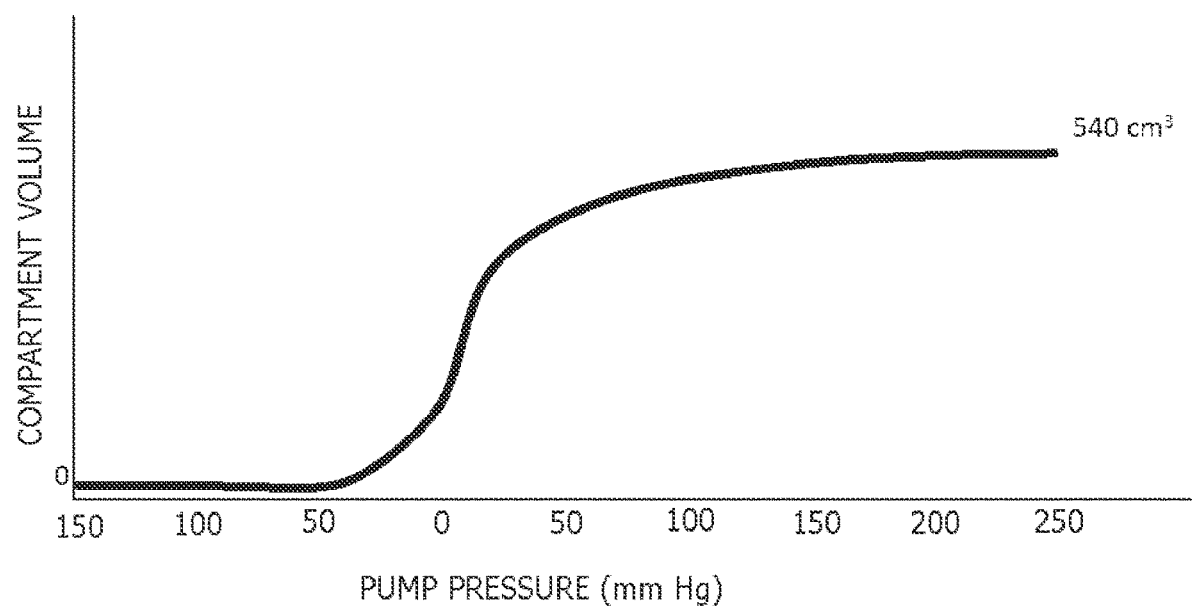
FIG. 5 is a graph that illustrates the change in volume in a compartment as a function of pressure change from the external automated drive.

The compartment membrane 20 is made of elastomeric material that expands and contracts as different pressures are applied. Accordingly, the volume of the underlying compartment 18 dynamically changes with changes in pneumatic pressure. Referring to FIG. 4 and FIG. 5 in conjunction with FIG. 2 and FIG. 3, it can be understood that each compartment 18 has a given volume at ambient pressure. The volume increases significantly when the compartment 18 experiences a positive pressure and decreases slightly in volume when a negative pressure is applied. The changes in volume over time correspond to the change in shape of the compartment 18. The change in shape over time of the compartment 18 can be expressed as the dynamic strain ε(t) of the compartment.

The compartment 18 is a three-dimensional construct that experiences strain in multiple directional planes that include a long axis plane 26 and a short axis plane 28. The long axis plane 26 would be the long axis of the heart's ventricular surface for which the cuff is intended to act upon. The short axis plane 28 would be the short axis plane of the heart's ventricular surface for with the heart cuff 12 is intended to act upon. Strains also occur in a radial axis plane. The radial axis plane would be the radial axis of the heart's ventricles for which the cuff is intended to act upon. Measurements of strains along the long axis plane 26 and the short axis plane 28 can be used as surrogates in estimating the overall three-dimensional strains. The long axis plane 26 extends generally vertically through the center of the compartment membrane 20. The short axis plane 28 extends generally horizontally through the center of the compartment membrane 20. Accordingly, the long axis plane 26 and the short axis plane 28 are perpendicular, or near perpendicular planes that are within five degrees of perpendicular. When in an unloaded condition, the compartment membrane 20 in the long axis plane 26 and in the short axis plane 28 have initial lengths at ambient pressure. As the compartment membrane 20 expands and contracts, there is a change in length (ΔL). This change in length translates to dynamic strain ε(t), as is later explained.

Figure 6:
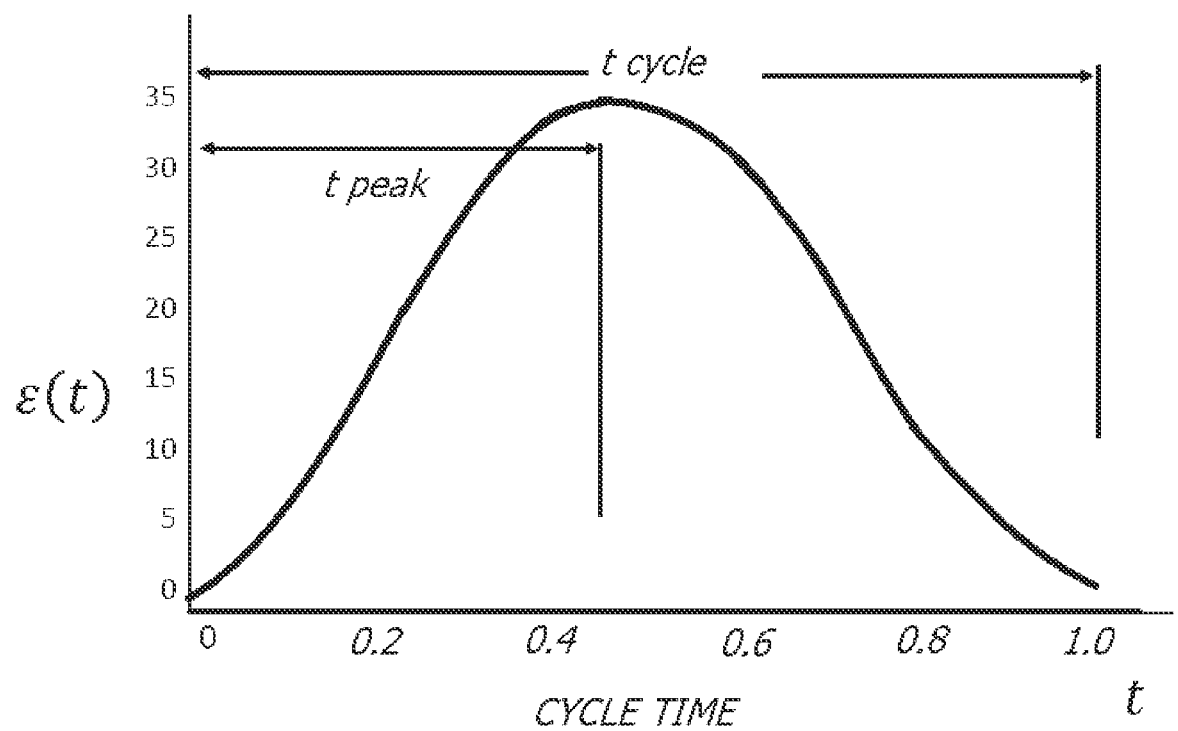
FIG. 6 is a graph that illustrates an example strain profile of an unloaded cuff across one beating cycle.

It will be understood that the compartment membrane 20 will be exposed to positive pressures and negative pressures in a manner that corresponds to the beating rhythm of a heart. Referring to FIG. 6 in conjunction with FIG. 1 and FIG. 2, a typical ventricular strain profile for an average human heart is shown, wherein the heart is average size and morphology for the adult human population. Such a ventricular strain profile can be generated for any heart of a given AV diameter. As can be seen, the dynamic strain ε(t) has a compression phase and a retraction phase 40 over time (t). As can also be seen, there is a peak strain $\varepsilon_{(peak)}$, a time to peak strain $t_{(peak)}$, and an overall cycle period $t_{(cycle)}$.

The elastomeric compartment membranes 20 of the heart cuff 12 apply direct forces to the heart 11 since the compartment membranes 20 physically contact with the heart 11. The shell 13 of the heart cuff 12 applies forces indirectly to the heart 11 since the shell 13 does not directly contact the heart 11 and forces are transferred through the elastomeric compartment membranes 20. The combined forces provided by the shell 13 and compartment membranes 20 and automated drive should optimally produce an ideal strain in the heart 11 that does not damage the heart and assists the heart in achieving an optimal heart pumping functionality. An ideal strain $\varepsilon_{(t)}$ characteristic can be estimated using the following equation:

Equation 2

$$\text{Strain} = \varepsilon(t) = \frac{\Delta L}{L_0} = \begin{cases} \frac{\varepsilon_{peak}}{2}\left(\sin\left(\frac{\pi}{t_{peak}} \times t - \frac{3}{2}\pi\right) - 1\right) \\ \frac{\varepsilon_{peak}}{2}\left(\sin\left(\frac{\pi}{t_{cycle} - t_{peak}} \times (t - t_{peak}) - \frac{\pi}{2}\right) - 1\right) \end{cases}$$

Figure 7:
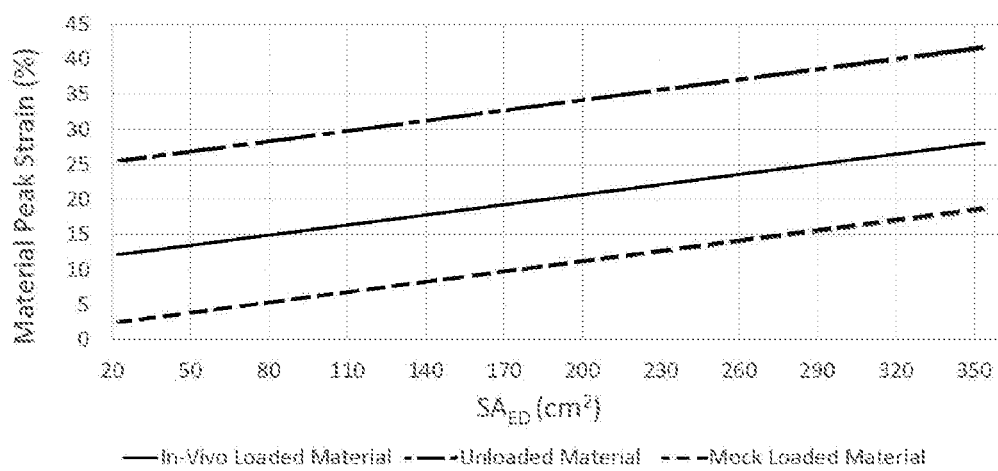
FIG. 7 is a graph of material peak strain verses surface area with results for an unloaded condition, an in vivo loaded condition and a mock loaded condition.

This ideal strain characteristic can be converted into a practical value for validation or testing in a construct that is being used either ex vivo in an unloaded condition, in vivo in a loaded condition, and/or in a mock loaded condition. Referring to FIG. 7, it will be understood that the ideal strain ε(t) can be converted into peak strain $\varepsilon_{(peak)}$ for an unloaded condition using Equation 3 below:

$\varepsilon_{peak} \approx 0.0481(SA_{ED}) + 24.496$    Equation 3

This value can be adjusted by +/−10% depending upon variabilities pertaining to intended surface area of the heart or the number of cuff compartments being tested.

The ideal strain ε(t) can be converted into peak strain $\varepsilon_{(peak)}$ for an in vivo loaded condition using Equation 4 below:

$\varepsilon_{peak} \approx 0.0481(SA_{ED}) + 11.064$    Equation 4

This value can be adjusted by +/−10% depending upon testing variables.

Lastly, the ideal strain ε(t) can be converted into peak strain $\varepsilon_{(peak)}$ for a mock loaded condition, i.e. use on a model, using Equation 5 below:

$\varepsilon_{peak} \approx 0.0481(SA_{ED}) + 1.496$    Equation 5

This value can be adjusted by +/−10% depending upon physical variability of the mock system utilized for testing.

Figure 8:
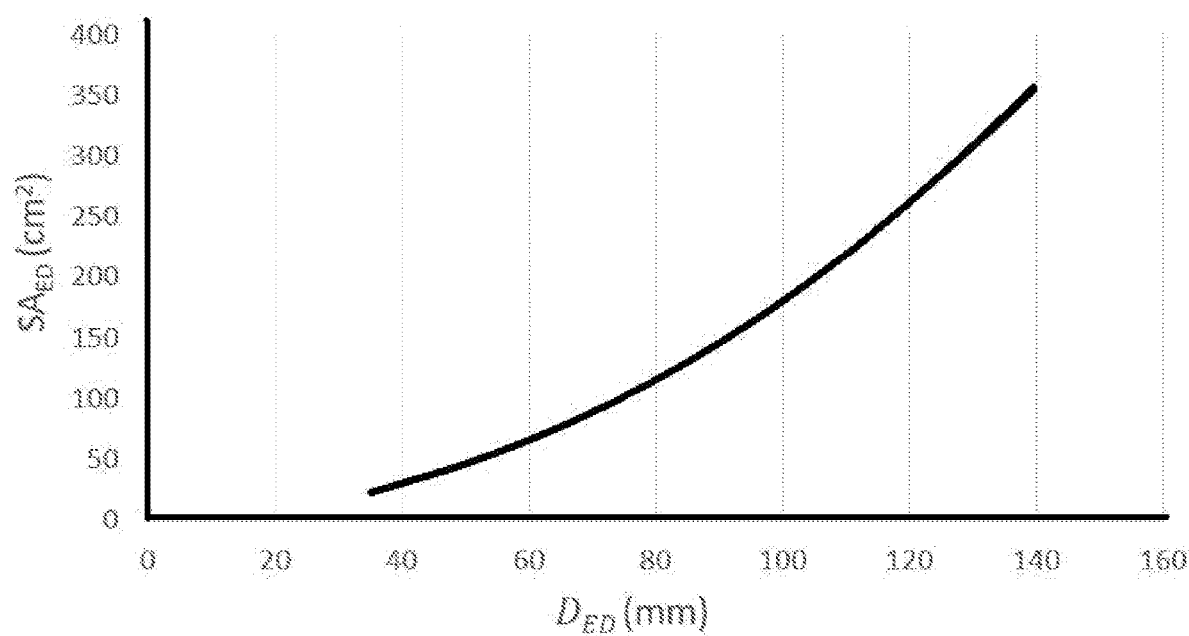
FIG. 8 is a graph that illustrates the relationship between active membrane surface area in relation to the maximal diameter of the heart at the end of the diastolic cycle.

For Equation 3, Equation 4 and Equation 5, the variable $SA_{ED}$ is the surface area of the compartment membrane 20 at the end of the diastolic cycle. To get a result from any of the equations, a value for $SA_{ED}$ must be obtained. As can be seen from FIG. 8, the surface area of the compartment membrane 20 at the end of the diastolic cycle $SA_{ED}$ is a function of the maximal diameter $D_{max}$ of the patient's heart at the end of the diastolic cycle. Accordingly, by measuring the maximal diameter $D_{max}$ of the patient's heart at the proper cycle time, the needed surface area $SA_{ED}$ of the compartment membrane 20 becomes known.

Referring back to FIG. 1, FIG. 3, and FIG. 4, it will be understood that good estimates of the dynamic strain profile of the heart cuff 12 can be accurately estimated by knowing the strains acting in the long axis plane 26 and in the short axis plane 28 of the compartment membrane 20. The strain in the long axis plane 26 is the longest vertical deformation of the compartment membrane 20 between the basal attachment seam 22 and the apical attachment seam 24. The short axis plane 28 is the longest horizontal path over the compartment membrane 20. The degree of deformation in the long axis plane 26 and in the short axis plane 28 both depend upon the pressures supplied by the external automated drive 14. However, the pressure supplied by the external automated drive 14 may be changed to a cycle that matches the rhythmic beat of the heart 11 depending on the functioning of the heart.

Figure 9:
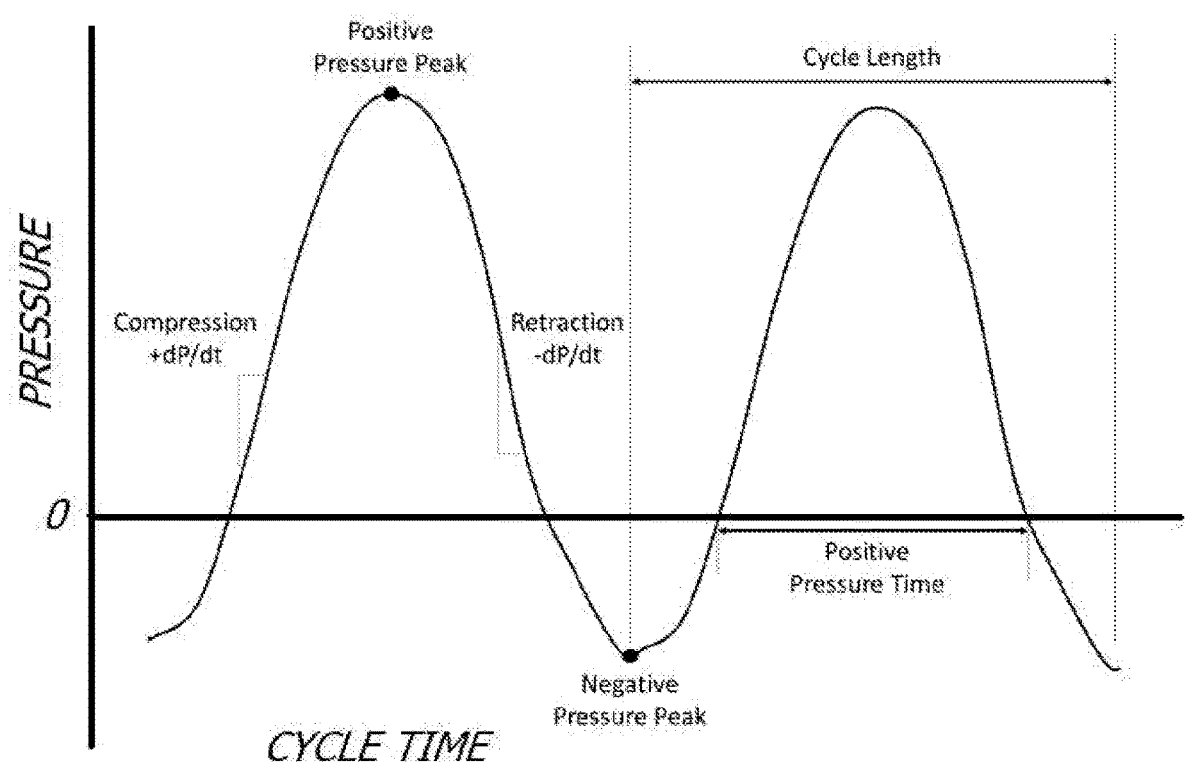
FIG. 9 is a graph that illustrates the changes in pressure experienced by the heart cuff in operation.

Referring to FIG. 9, it can be seen that the pressures supplied to the compartment membrane 20 by the external automated drive have a maximum pressure $P_{max}$, a minimum pressure $P_{min}$, a cycle time $T_{cycle}$, and a pressure range $P_{range}$, which is the difference between the maximum pressure $P_{max}$ and the minimum pressure $P_{min}$ during the cycle time $T_{cycle}$. Given these parameters the pressure P(t) on the compartment membrane at any time (t) in the cycle time can be calculated using Equation 6 below:

$$P(t) = \begin{cases} \frac{P_{range}}{2} \sin\left(\frac{\pi}{t_{peak}} \times t - \frac{\pi}{2}\right) - 2(P_{min}) & 0 \leq t < t_{peak} \\ (P_{range}) \sin\left(\frac{\pi}{t_{cycle} - t_{peak}} \times (t - t_{peak}) - \frac{3}{2}\pi\right) - P_{min} & t_{peak} \leq t < t_{cycle} \end{cases}$$

Equation 6

Once the pressure $(P_t)$ is calculated, the stress experienced by an unloaded compartment membrane 20 in both the long axis plane 26 and the short axis plane 28 can be calculated.

The first step in calculating strain in the long axis plane 26 and in the short axis plane 28 is to use the pressure (P) to determine the maximum strain in the long axis plane 26 and in the short axis plane 28. The maximum strain $\varepsilon_{(peak-LA)}$ in the long axis plane 26 is determined by Equation 7 below:

$$\varepsilon_{peak-LA} = 11.676 \ln(P) - 5.2073 \quad \text{Equation 7}$$

The maximum strain $\varepsilon_{(peak-SA)}$ in the short axis plane 28 is determined by Equation 8 below:

$$\varepsilon_{peak-SA} = 6.5167 \ln(P) - 5.1506 \quad \text{Equation 8}$$

Again, the values generated by Equation 7 and Equation 8 can vary by up to 5% depending on testing platform and area of material and/or compartments used in the cuff. Once the peak strains are calculated in the long axis plane 26 and in the short axis plane 28, the dynamic strains can be calculated. The dynamic strain $\varepsilon_{(x)}$ for the long axis plane 26 is determined by Equation 9 below:

$$\varepsilon(x) = \quad \text{Equation 9}$$
$$\frac{\varepsilon_{peak-LA}}{40.8}(4 \times 10^{-6}x^4 - 0.0008x^3 + 0.0324x^2 + 0.6868x - 0.4757)$$

The dynamic strain $\varepsilon_{(x)}$ acting in the short axis plane 28 is determined by Equation 10 below:

$$\varepsilon(x_{SA}) = \frac{\varepsilon_{peak-SA}}{20.1}(-0.00005x^3 + 0.0004x^2 + 0.5171x + 0.0052) \quad \text{Equation 10}$$

In view of the equations provided above, the strain profile for the compartment membrane 20 in the heart cuff 12 are calculated in both the long axis plane 26 and in the short axis plane 28.

Using the above, the strain profile for the compartment membrane 20 is calculated in both the long axis plane 26 and in the short axis plane 28 assuming an unloaded condition. This is highly useful in creating an elastomeric construct that will function very close to what is needed. However, once the elastomeric construct is loaded, that is applied to the heart, actual strain features can be determined by measurements during trial and error.

The strain dynamics embodied by the elastomeric material of the heart cuff 12 can be selectively altered by changing the thickness and/or material properties of the elastomeric material used in the heart cuff 12. The value for the dynamic strain applied by the external automated drive 14 can be controlled to some degree by active programming. However, certain variables, such as the rate that pressure can be increased and decreased is limited by the hardware being used. Accordingly, using the present invention methodology, a designer now has the ability to program the external automated drive 14 to settings that are the closest to ideal.

The final changes in strain that are unachievable by programming can be achieved by altering the physical characteristics of the compartment membrane 20. By altering the elastomeric material used in the construction of the compartment membrane 20 and optimizing the programming of the external automated drive 14, the combined factors can create a dynamic strain profile that reinforces the heart 11 and enable the heart to pump in a more optimal manner.

Referring to all figures, it will be understood that the first step in determining what heart cuff 12 to use and what programming to use on the external automated drive 14 is to determine the dynamic strain profile for an average heart with generally normal morphology. The actual dynamic strain profile for the heart is measured using known techniques. The patient's heart may be in full or partial failure. The difference between the dynamic strain profile of the actual heart 11 and the dynamic strain profile of an average heart with generally normal morphology are determined. It is this difference that has to be compensated for using the heart cuff 12.

A heart cuff 12 is selected having a dynamic strain profile that was estimated and/or measured in an unloaded condition and extrapolated for the loaded condition. The heart cuff 12 is then loaded. That is, placed into contact with the heart 11. If the strain dynamics embodied by the heart cuff 12 does not provide the pumping assist needed, then the heart cuff 12 is altered or is replaced by another heart cuff that is better suited to the circumstances. The strain characteristics of the heart cuff 12 can be altered by altering the elastomeric material used in the shell 13 and compartment membranes 20 of the heart cuff 12. The elastomeric material can be made thicker and/or thinner in various places. Other variables, such as the hardness, tensile strength, tensile modulus, elongation, resilience, compression set, and specific gravity can also be altered to change the dynamic strain profile of the heart cuff.

Once the dynamic strain profile of the heart cuff 12 is altered, the altered heart cuff can again be tested. This cycle of alteration and checking can be repeated until the dynamic strain profile embodied by the heart cuff 12 matches what is needed by the actual heart in order to enable the heart to pump more in a more effective manner.

Figure 10:
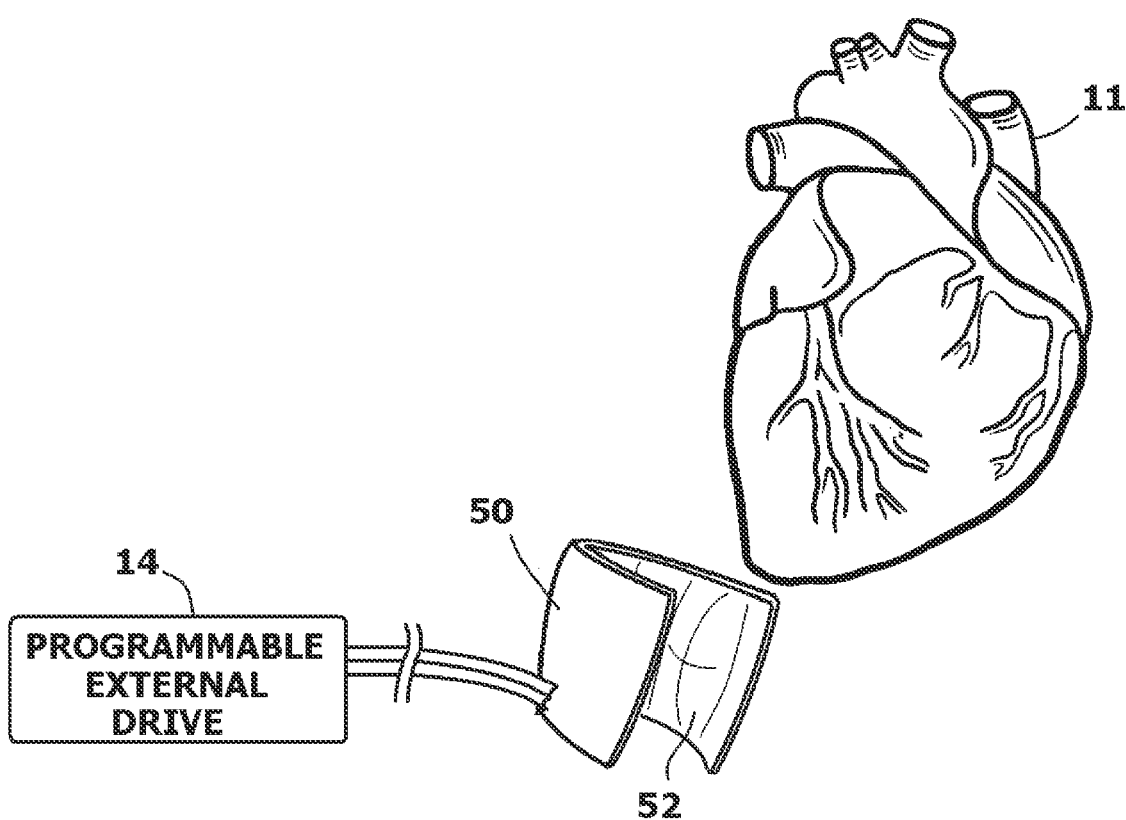
FIG. 10 is a schematic of an exemplary embodiment of a heart pump system showing a heart in conjunction with a partial heart cuff.

In the illustrated embodiment, the heart cuff 12 encircles the heart. It will be understood that there are many elastomeric constructs that are selectively inflated with pneumatic pressure, that do not encircle the heart. Rather, such devices typically press against only one area of the heart or are positioned internal of the heart. Referring to FIG. 10, a partial cuff 50 is shown. The partial cuff 50 can be positioned to apply forces to only the left ventricle, the right ventricle or portions thereof. Such partial cuffs can be used when scar tissue or other abnormalities prevent the application of a full cuff. Such partial cuffs are also easier to use during non-invasive procedures. Regardless, the partial cuff 50 contains one or more elastomeric constructs 52 that apply forces to the heart 11. The methodology previously described for use of a full cuff is still valid for use on a partial cuff. Accordingly, the system and method described for full cuffs apply equally to partial cuffs or even smaller inflatable constructs. All such constructs are intended to be covered within the scope of the claims.

It will be understood that the embodiments of the present invention that are illustrated and described are merely exemplary and that a person skilled in the art can make many variations to those embodiments. All such embodiments are intended to be included within the scope of the present invention as defined by the claims.

What is claimed is:

1. A method of determining strain characteristics for a construct being applied to a heart, said method including:
   determining a set of strain characteristics required to be applied to the heart to provide an assist the heart that causes the heart to pump in a more efficient manner;
   providing a construct with elastomeric elements, wherein each of said elastomeric elements expands along multiple axes when internally pressurized, and wherein said multiple axes include a first axis and a second axis;
   in an unloaded condition remote from the heart, internally pressurizing said elastomeric elements to determine a pressure differential experienced by said elastomeric elements within said construct;
   in said unloaded condition, calculating a first strain characteristic along said first axis as a function of said pressure differential by multiplying a log of said pressure differential times a first constant and subtracting a second constant;
   in said unloaded condition, calculating a second strain characteristic along said second axis as a function of said pressure differential;
   utilizing said first strain characteristic and said second strain characteristic to estimate dynamic strain characteristics to be applied by said construct;
   comparing said dynamic strain characteristics estimated for said construct to said set of strain characteristics to determine if said construct will assist the heart in pumping;
   placing said construct into contact with the heart in vivo; and
   operating said construct to determine if said construct provides said assist to the heart.

2. The method according to claim 1, wherein calculating said second strain characteristic along said second axis includes multiplying a log of said pressure differential times a first constant and subtracting a second constant.

3. The method according to claim 1, where said first axis is angled relative to said second axis.

4. The method according to claim 1, wherein said first strain characteristic is a function of a first peak strain measured along said first axis.

5. The method according to claim 4, wherein said second strain characteristic is a function of a second peak strain measured along said second axis.

6. The method according to claim 5, wherein said first peak strain along said first axis ($\varepsilon$peak-LA) is calculated using the formula $$\varepsilon_{peak-LA} = 11.676 \ln(P) - 5.2073$$

where (P) is said pressure differential.

7. The method according to claim 6, wherein said first strain characteristic ($\varepsilon$x) is calculated using the formula $$\varepsilon(x) = \frac{\varepsilon_{peak-LA}}{40.8}\left(4 \times 10^{-6} x^4 - 0.0008 x^3 + 0.0324 x^2 + 0.6868 x - 0.4757\right)$$

where ($\varepsilon$peak-LA) is said first peak strain along said first axis.

8. The method according to claim 5, wherein said second peak strain along said second axis ($\varepsilon$peak-SA) is calculated using the formula $$\varepsilon_{peak-SA} = 6.5167 \ln(P) - 5.1506$$

where (P) is said pressure differential.

9. The method according to claim 8, wherein said second strain characteristic ($\varepsilon x_{SA}$) is calculated using the formula $$\varepsilon(x_{SA}) = \frac{\varepsilon_{peak-SA}}{20.1}\left(-0.00005 x^3 + 0.0004 x^2 + 0.5171 x + 0.0052\right)$$

where ($\varepsilon$peak-SA) is said second peak strain along said second axis.

10. A method of determining if a pumping construct assists a heart in pumping, said method including:
   determining required dynamic forces that need to be applied to the heart to provide an assist to the heart that helps the heart pump in a more effective manner;
   providing said pumping construct, wherein said pumping construct has elastomeric elements that expands when internally pressurized, and wherein each of said elastomeric elements has a first axis and a second axis;
   internally pressurizing said elastomeric elements to determine a pressure differential experienced by said elastomeric elements within said pumping construct when said elastomeric elements are not in contact with the heart;

measuring said elastomeric elements to obtain deformation measurements as elastomeric elements are internally pressurized, wherein said deformation measurements include a first peak strain measurement along said first axis and a second peak strain measurement along said second axis, and wherein said first peak strain measurement is a log of said pressure differential times a first constant and subtracting a second constant;

utilizing said deformation measurements and said pressure differential to estimate applied dynamic forces;

comparing said applied dynamic forces estimated for said pumping construct to said required dynamic forces to determine if said pumping construct can assist the heart in pumping;

placing said pumping construct into contact with the heart in vivo; and operating said pumping construct to determine if said pumping construct provides said assist to the heart.

11. The method according to claim 10, further including calculating said second peak strain measurement along said second axis by multiplying a log of said pressure differential times a third constant and subtracting a fourth constant.

12. The method according to claim 11, wherein said first peak strain measurement and said second peak strain measurement are used to estimate said applied dynamic forces.

13. The method according to claim 12, wherein said first peak strain measurement along said first axis ($\varepsilon$peak-LA) is calculated using the formula $$\varepsilon_{peak-LA} = 11.676 \ln(P) - 5.2073$$

where (P) is said pressure differential.

14. The method according to claim 13, wherein said first peak strain measurement ($\varepsilon$x) is calculated using the formula $$\varepsilon(x) = \frac{\varepsilon_{peak-LA}}{40.8}(4 \times 10^{-6} x^4 - 0.0008 x^3 + 0.0324 x^2 + 0.6868 x - 0.4757)$$

where ($\varepsilon$peak-LA) is said first peak strain measurement along said first axis.

15. The method according to claim 12, wherein said second peak strain measurement along said second axis ($\varepsilon$peak-SA) is calculated using the formula $$\varepsilon_{peak-SA} = 6.5167 \ln(P) - 5.1506$$

where (P) is said pressure differential.

16. The method according to claim 15, further including calculating a short axis strain ($\varepsilon x_{SA}$) using the formula $$\varepsilon(x_{SA}) = \frac{\varepsilon_{peak-SA}}{20.1}(-0.00005 x^3 + 0.0004 x^2 + 0.5171 x + 0.0052)$$

where ($\varepsilon$peak-SA) is said second peak strain measurement along said second axis.

* * * * *